United States Patent [19]

Abe et al.

[11] Patent Number: 4,908,443
[45] Date of Patent: Mar. 13, 1990

[54] 7-BETA-SUBSTITUTED 3-LOWER ALKANOYLACETOXY-METHYL-7-ALPHA-METHOXY-3-CEPHEM-4-CARBOXYLIC ACID

[75] Inventors: Masami Abe; Hideo Eiki, both of Ibaraki, Japan

[73] Assignee: Yamanouchi Pharmaceutical Co., Ltd., Tokyo, Japan

[21] Appl. No.: 356,607

[22] Filed: May 23, 1989

Related U.S. Application Data

[63] Continuation of Ser. No. 294,922, Jan. 5, 1989, abandoned, which is a continuation of Ser. No. 173,374, Mar. 25, 1988, abandoned.

[30] Foreign Application Priority Data

Mar. 31, 1987 [JP] Japan .................................. 62-79973

[51] Int. Cl.$^4$ .................. C07D 501/57; A61K 31/545
[52] U.S. Cl. ..................................... 540/221; 514/201; 435/119
[58] Field of Search ........................................ 540/221

[56] References Cited

PUBLICATIONS

Baldwin et al., JACS, vol. 95:7, Apr. 4, 1973.

*Primary Examiner*—Nicholas S. Rizzo
*Attorney, Agent, or Firm*—Burgess, Ryan and Wayne

[57] ABSTRACT

Novel cephem compounds are provided which are useful for synthesizing cephamycin compounds useful as antibacterial agents. The novel compounds have the formula (I):

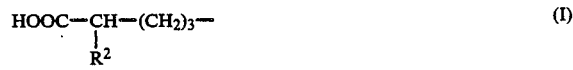
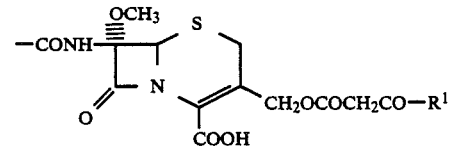

wherein $R^1$ represents a lower alkyl group and $R^2$ represents an amino group which may be protected, in the salt thereof.

1 Claim, No Drawings

7-BETA-SUBSTITUTED 3-LOWER ALKANOYLACETOXY-METHYL-7-ALPHA-METHOXY-3-CEPHEM-4-CARBOXYLIC ACID

This application is a continuation of application Ser. No. 294,922, filed 1/5/89, which is a continuation of U.S. No. 173,374 filed 3/25/88, now abandoned.

BACKGROUND OF THE INVENTION

1. Field of the Invention

The present invention relates to an intermediate compound useful for synthesizing cephamycin compounds useful as antibacterial agents and to a process for production of the same. More particularly, the present invention provides 7β-substituted-3-lower alkanoylacetoxymethyl-7α-methoxy-3-cephem-4-carboxylic acid represented by following general formula (I):

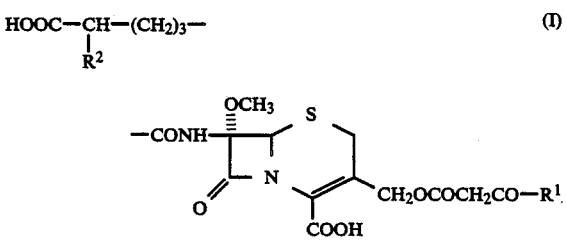

wherein $R^1$ represents a lower alkyl group and $R^2$ represents an amino group which may be protected, and a salt thereof.

The present invention also provides a process for producing the compound shown by general formula (I) which comprises culturing bacteria which belong to the genus Streptomyces and are capable of producing a cephamycin compound represented by following general formula (II):

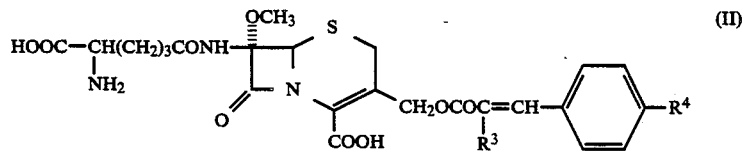

wherein $R^3$ represents a hydrogen atom or a methoxy group and $R^4$ represents a hydroxy group or a sulfoxy group, allowing yeast belonging to the genus Torulopsis, or esterase derived from the yeast or material containing this esterase, to act on the accumulated cephamycin compound of general formula (II) in the culture solution to form 7β-(D-5-amino-5-carboxyvaleramido)-3-hydroxymethyl-7α-methoxy-3-cephem-4-carboxylic acid (hereafter simply referred to as "oganomycin E") of following formula (III):

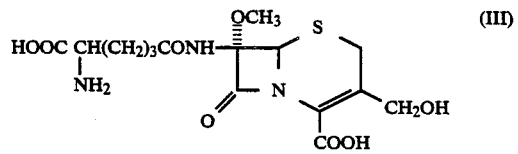

or a salt thereof (fermentation production step); reacting the oganomycin compound of formula (III) (optionally with its amino group protected) with a lower alkanoylacetic acid or a reactive derivative thereof (chemical process step); and optionally removing a protective group and/or converting to or from salt form.

The compounds according to this invention are novel and there is no published report on them. A characteristic feature of the claimed compounds in terms of chemical structure resides in the fact that the lower alkanoylacetoxymethyl group is present at the 3-position of the cephalosporin ring. The compounds of the present invention can easily be prepared employing as an intermediate compound oganomycin E which can be produced in high yield by our novel fermentation process found by the present inventors et al.

2. Background of the Invention

Known methods for producing oganomycin E by fermentation methods include culturing Streptomyces chartreusis SF-1623 under aerobic conditions and harvesting the compound from the culture solution (published unexamined Japanese patent application No. 121488/1975) and culturing Streptomyces oganonensis and harvesting the compound from the culture solution (published unexamined Japanese patent application No. 43697/1982).

However, the former method gives a low yield and is unsuitable for industrial production. The latter method provides at least 1000 times the yield but the concentration of oganomycin E accumulated in the culture solution is approximately 5 mg/ml.

SUMMARY OF THE INVENTION

As a result of extensive investigation to achieve a higher product concentration, the present inventors have found that by incorporating yeasts belonging to the genus Torulopsis in some fermentation media and culturing them, accumulated quantities of oganomycin E can be increasingly enhanced.

Our method for producing oganomycin E by fermentation involves culturing oganomycin E-producing bacteria and harvesting directly oganomycin E of formula (III) accumulated in the culture solution, and producing cephamycin compounds of general formula (II) analogous to oganomycin E by fermentation and hydrolysing the ester of the cephamycin compound to form oganomycin E. We have found that yeasts belonging to the genus Torulopsis and esterase derived therefrom can easily hydrolyse the ester at the 3-position of cephamycin compounds of general formula (II) to efficiently convert to oganomycin E.

The compounds of general formula (I) according to the present invention can then be produced by chemically treating oganomycin E which is efficiently prepared by the fermentation methods as above-mentioned.

DETAILED DESCRIPTION OF THE INVENTION

The fermentation production and chemical process steps of the present invention are discussed separately and in greater detail below.

1. FERMENTATION PRODUCTION STEP

This step includes culturing cephamycin compounds of formula (II)-producing bacteria and allowing yeasts belonging to the genus Torulopsis or esterase derived therefrom or material containing the esterase to act on accumulated cephamycin compound in the culture solution to form oganomycin E. Examples of bacteria capable of producing cephamycin compounds of formula (II) which can be used in the present invention include *Streptomyces griseus* MA-2837 and MA-4125a (Published unexamined Japanese patent application No. 3286/1971), *Streptomyces viridochromogenes, Streptomyces fimbriatus, Streptomyces halstedii, Streptomyces rochei, Streptomyces cinnamonensis* and *Streptomyces chartreusis* (Belgian Pat. No. 764,160). Further, *Streptomyces oganonensis* Y-G19Z by-produces cephamycin compounds of formula (II) and thus can also be listed as a cephamycin compound-producing bacterium (Published unexamined Japanese patent application No. 79394/1980). The cephamycin compounds of formula (II) produced by these micro-organisms are specifically cephamycin A ($R^3$=—$OCH_3$, $R^4$=—$OSO_3H$), cephamycin B ($R^3$=—$OCH_3$, $R^4$=—OH), oganomycin A ($R^3$=—H, $R^4$=—$OSO_3H$), oganomycin B ($R^3$=—H, $R^4$=—OH), etc.

The esterase derived from yeasts belonging to the genus Torulopsis which can be employed in the present fermentation production step is an enzyme capable of hydrolysing the ester bond at the 3-side chain of said cephamycin compounds of formula (II). Material containing the aforementioned esterase may be in any form carrying the same, and examples of such material are micro-organisms carrying the esterase, immobilized esterase, etc.

As a result of investigation on various microorganisms isolated from the soil, the present inventors have found that the aforementioned esterase which can hydrolyse the 3-side chain ester of cephamycin compounds of formula (II) is present in a genus of yeast. One suitable yeast strain has various properties as follows:

(1) MORPHOLOGICAL PROPERTY

Vegetative cells are spherical or oval, sometimes protractile in various media. The size is 3.0 to 10 μm×2.0 to 5 μm with oval cells and 3 to 11 μm with spherical ones.

Vegetative propagation occurs by multipolar budding. Formations of Pseudomycelia, chlamydospore, oidispore, budding spore, etc. are absent but a trace of pseudomycelia-like formation sometimes occurs. Neither ascospores nor balistospores are formed.

(2) CULTURING PROPERTIES (cultured at 25° C. for 3 to 14 days)

[1] Maltose Medium

The medium is somewhat turbid as a whole and colored pale pink to light orange. Neither skin nor precipitate is formed. Generation of gas is not observed.

[2] Potato Dextrose Agar

Colonies are smooth, glossy, colored pale orange to light orange and rise to a hemispherical shape on agar. No diffusible dye is noted.

(3) PHYSIOLOGICAL PROPERTIES

[1] Fermentation of glucose is weak but positive. Fermentation of fructose, galactose, sucrose, maltose and raffinose is negative.

[2] Utilization of Carbon Source (cultured at 25° C. for 21 days)

Maltose—
D-Galactose+
Fructose—
Glucose+
L-Arabinose+
D-Xylose+
Sucrose—
Inositol—
L-Ramnose—
L-Raffinose—
Mannitol—
Lactose+
D-Sorbitol—
Salicine+
Glycerine+
+: utilized
—: not utilized

[3] Assimilation of Nitrates: Positive

[4] Formation of Starch-like Substance: Negative

[5] Formation of Carotinoid Dye: Negative (bacterial dye is a non-carotinoidal substance insoluble in acetone and petroleum ether)

[6] Formation of Ester: Negative

[7] Acid-formation: Negative

[8] Decomposition of Oils and Fat: Negative

[9] Vitamin Auxotrophy: None

[10] Growth Temperature:
It grows at 10° to 33° C. but does not grow at 5° C. and 37° C.

[11] Urease: Positive

In summary, this strain belongs to a non-spored yeast; nutrient cells are spherical or oval; and pseudo-mycelia are sometimes observed as traces; no starch-like substance is formed but assimilation of nitrates is positive; neither skin nor precipitate is formed by liquid culture; colonies are colored pale orange to light orange but this dye is not of carotinoid; further fermentation of glucose is weak but positive. Upon examination of the literature, genera of microorganisms having these properties are the genus Cryptococcus and the genus Torulopsis which are characterized as a non-spored yeast, forming intracellular non-carotinoid dye, propagating in spheral or oval multipolar buds and neither forming oidispore nor pseudomycelia. The former is covered with a capsule, colonies are viscous and starch-like substance is formed. This strain does not show such properties and hence is distinguishable. On the other hand, in comparison with the latter, the morphological properties, physiological properties, etc. of the present strain correspond closely with those of yeasts belonging to the genus Torulopsis. The new strain has been named the type strain Torulopsis sp. YE-0807L accordingly. The type strain has been deposited in the Agency of Industrial Science and Technology, the Fermentation Research Institute under the accession number FERM BP-1158.

The properties of the type strain isolated by the present inventors have been described hereinabove. In addition to this strain, other yeasts of genus Torulopsis carrying or producing the esterase or treated products thereof can also be employed in the present invention.

For the present purposes, yeasts are a good group of micro-organisms as compared to, e.g. bacteria and molds, since they do not inhibit the fermentation metabolism system and can achieve optimum conditions. This is particularly important in the case of adopting a so-called mixing culture method in which several microorganisms are co-cultured, e.g. cephamycin compound-producing bacteria are cultured in the presence of esterase-producing micro-organisms to produce oganomycin E. Other esterase-producing microorganisms may have a potent productivity of amylases or proteases, they may have a potent productivity of acidic substances or basic substances, or they may have a large propagation rate or oxygen absorption rate, etc.; these may disrupt the fermentation metabolism environment and hence reduce the total product yield of oganomycin E. Accordingly, such other micro-organisms are not suitable for the present invention.

According to the present invention, oganomycin E can be prepared as follows:

PROCESS 1 (mixing fermentation method)

In the mixing fermentation method, a cephamycin compound-producing strain is cultured under culturing conditions for the production of the cephamycin compounds by fermentation and yeast belonging to the genus Torulopsis is inoculated and both strains are simultaneously cultured. That is, deep culture using liquid medium is advantageous. In the mixing fermentation method it is possible that the esterase acts in a contaminated bacteria-free environment, and hence this method is a preferable embodiment in the present invention.

Hereafter the mixing fermentation method will be described in more detail below.

The medium used for the mixing culture may be any medium as far as it contains nutrient sources that the cephamycin compound-producing bacteria belonging to the genus Streptomyces can utilize. Thus, a synthetic medium, semi-synthetic medium or natural medium can be used. In such a medium, glucose, sucrose, mannitol, glycerine, dextrin, starch, vegetable oils, etc. are used as carbon sources and meat extract, peptone, gluten meal, cotton seed lees, soybean powders, peanut powders, fish powders, corn steep liquor, dry yeast, yeast extract, ammonium sulfate, ammonium nitrate, urea and other organic or inorganic nitrogen sources are employed as nitrogen sources. Further metal salts, e.g. sulfates, nitrates, chlorides, carbonates, phosphates, etc. of Na, K, Mg, Ca, Zn, Fe, etc. may be incorporated, if necessary or desired. In particular, the incorporation of magnesium carbonate is effective for increasing the productivity (titer) of oganomycin E of formula (III). Further, if necesssary or desired, antibiotic production-accelerating substances or defoaming agents such as methionine, cysteine, cystine, methyl oleate, lard oil, silicone oil, surfactants, etc. may be used.

It is generally advantageous to culture under aerobic conditions. It is desired that the culturing temperature is in a range of about 18° to about 35° C., preferably about 30° C. Good results are obtained when the pH of the medium is kept in a range of about 5 to about 10, preferably about 6 to about 8. The period for incubation varies depending upon composition of the medium, temperature, etc. but is generally about 3 to about 10 days. Inoculation of the yeast belonging to the genus Torulopsis producing the esterase at an initial stage of the culture is effective. Good results may be obtained when inoculation of the yeast is at the time of initiating the culture or up to the second day. When using the esterase or materials containing the same instead of the yeast, it may be aseptically incorporated prior to the production of the cephamycin compound of formula (II); alternatively, the culture solution containing the cephamycin compound of formula (II) may be cycled to a reactor containing the esterase.

PROCESS 2 (enzymatic hydrolysis of cephamycin compounds of formula (II))

This process comprises using cephamycin compound of formula (II) as a substrate, and allowing yeast belonging to the genus Torulopsis, or the esterase produced therefrom or material carrying the same, to act thereon to produce oganomycin E. To perform this process, yeast belonging to the genus Torulopsis, or the esterase produced therefrom or material carrying the same can be mixed with a solution of the cephamycin compound of formula (II); the mixture is shaken at about 30° C. at neutral pH, and the formed oganomycin E is separated. As the solution of the cephamycin compound of formula (II), there may be used any of a fermentation solution containing the compound of formula (II), a fermentation filtrate or a solution of the cephamycin compound of formula (II) separated and isolated. As the esterase source, there can be utilized a culture solution per se of the yeast belonging to the genus Torulopsis, cells of a yeast, ground cells, an extract of the esterase active fraction, or solid carriers (activated charcoal, diatomaceous earth, hydrophilic gel, high molecular resins, etc.) having immobilized thereon esterase or yeast carrying the same.

To isolate and harvest oganomycin E of formula (III) from the culture, there may be adopted conventional method for isolating antibiotics from the culture of micro-organisms. Oganomycin E of formula (III) is mainly contained in the culture solution and therefore micro-organism cells can be removed by centrifugation or filtration and thereafter oganomycin E extracted from the filtrate. Namely, oganomycin E can be separated, harvested and purified by methods used for production of ordinary antibiotics utilizing a difference in solubilizing property or solubility in an appropriate solvent, a difference in precipitating property or precipitating rate from a solution, a difference in adsorptive affinity to various adsorbents, a difference in distribution between two liquid phases, etc.

These isolating methods can be applied singly, in any combination in any order, or repeatedly, if necessary or desired.

In the process of the present invention, oganomycin E may be obtained as a free acid or a salt such as a usual alkali metal salt (e.g., Li-, Na-, K-salts), an alkaline earth metal salt (e.g., Ca-, Mg-, Ba-salts), an organic amine salt (e.g., triethylamine salt), etc.

2. CHEMICAL PROCESS STEP

The desired compound of formula (I) according to the present invention can be prepared by chemically treating oganomycin E obtained in the aforementioned fermentation production step.

This chemical process step is shown by the following reaction equations:

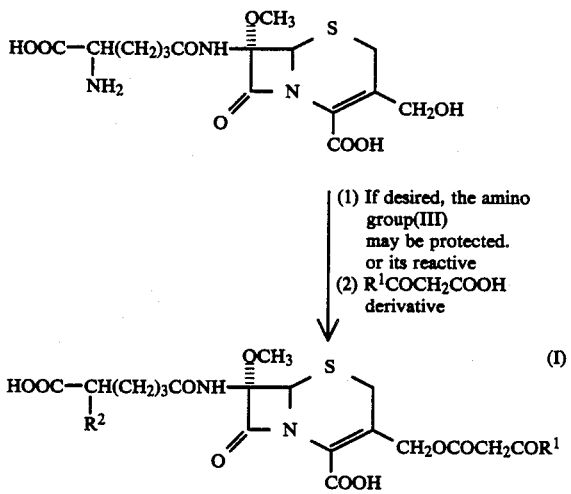

This process utilizes, as the raw material, oganomycin E of formula (III) obtained by the above-described fermentation production step, wherein the α-amino group at the 5-carboxy valeramide group of oganomycin E may be protected, if desired, and it is performed by reacting oganomycin E of formula (III) with a lower alkanoylacetic acid represented by general formula (IV):

$$R^1COCH_2COOH \qquad (IV)$$

wherein $R^1$ has the meaning as defined above, or a reactive derivative thereof.

Examples of the protective group for the amino group include aromatic acyl groups such as phthaloyl-, benzoyl-, p-nitrobenzoyl-, toluoyl-, benzenesulfonyl-, phenoxyacetyl groups, etc., N-carbamoyl group formed by reacting with arylisocyanate, etc.

Examples of lower alkanoylacetic acids shown by general formula (IV) are straight- or branched chain ($C_1$-$C_5$ alkanoyl) acetic acids such as acetoacetic acid, propionylacetic acid, butyrylacetic acid, valerylacetic acid, etc.

Further, examples of the reactive derivatives of the above alkanoylacetic acids include diketene, lower alkanoylacetic acid halides or acid anhydrides thereof, etc.

The reaction of the present process can be performed using lower alkanoylacetic acids of formula (IV) or reactive derivatives thereof in equimolar amounts or with slight excess of the raw material compound of formula (III). The reaction temperature is not specifically limited but ice-cooling or heating is preferred. Examples of the reaction solvent are inert solvents to the reaction such as dichloromethane, chloroform, dichloroethane, dimethylformamide, tetrahydrofuran, acetone, etc. To perform the reaction the 4-position carboxylic group may be protected, if necessary or desired; alternatively, any amine such as triethylamine, etc. may be added.

The resultant compound of formula (I) of this invention can be isolated as it is or as a salt thereof and purified. Isolation and purification can be effected employing conventional chemical operations such as extraction, crystallization, recrystallization, various kinds of chromatography, etc.

The effect according to the process of the present invention resides in that the 3-side chain ester of cephamycin compounds of formula (II) is enzymatically hydrolyzed to efficiently convert to oganomycin E and then the desired compound of formula (I) of this invention is industrially and cheaply produced using the aforesaid oganomycin E as the raw material. In particular, in the mixing fermentation method the cephamycin compound of formula (II) by-produced and accumulated in the culture medium can be converted to oganomycin E without isolation of said cephamycin compound effected and therefore a culture solution containing oganomycin E alone and at a high concentration can be obtained. Namely, the present fermentation production method can give an oganomycin E product concentration, 5 times greater than previous conventional methods and the resulting oganomycin E can be employed in the subsequent chemical treating process as the raw material. Thus, the present invention provides an industrially advantageous process.

The compound of formula (I) according to the present invention is also useful as an intermediate compound for producing cephamycin series compounds possessing superior antibacterial activity. That is, the present compound of formula (I) can be converted to cefotetan exhibiting excellent antibacterial activity according to the process shown by the following reaction equations:

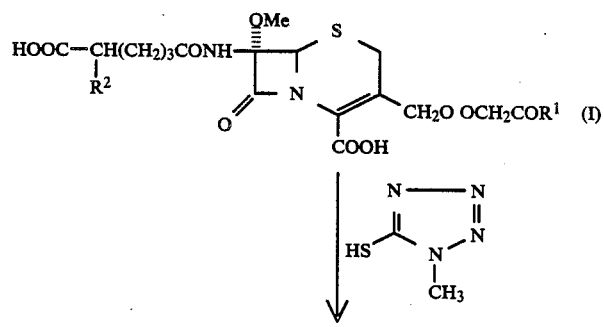

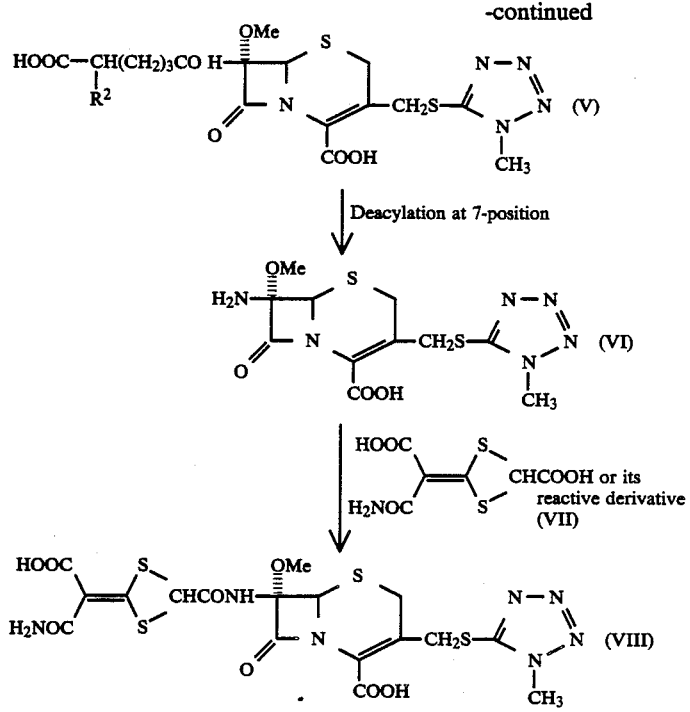

Cefotetan (Published examined Japanese patent application 11956/1983)

Namely, cefotetan having excellent antibacterial activity can be obtained by utilizing a desired compound of formula (I) of this invention as a starting material, substituting the 3-position lower alkanoylacetyloxy group of said compound for a (1-methyltetrazol-5-yl) thio group to give the compound of formula (V), removing the 7-position acyl group by means of hydrolysis to yield the compound of formula (VI), and reacting the compound (VI) with 4-(carbamoylcarboxymethylene)-1,3-dithiethan-2-sulfonic acid.

Next, the process of the present invention will be described in more detail with reference to the examples below. In these examples, Example (a) relates to production of oganomycin E according to the mixing fermentation production step, (b) to production of N-phthaloyloganomycin E and (c) to production of a desired compound of the present invention, respectively.

As a reference example, there is shown the first process step among the steps for converting a compound of formula (I) of this invention to cefotetan of formula (VIII).

EXAMPLE (a) (Production of oganomycin E by the mixing fermentation production method)

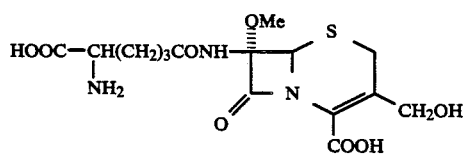

In a 500 ml Sakaguchi flask 100 ml of seed medium containing 1% starch, 1% glucose, 1.5% soybean powder, 0.5% yeast extract, 0.1% hydrogen disodium phosphate, 0.05% magnesium sulfate and 0.3% sodium chloride was charged, followed by sterilizing at 120° C. for 20 minutes. *Streptomyces oganensis* Y-G19Z was inoculated and cultured at 30° C. for 2 days. A 500 ml Erlenmeyer's flask charged with 50 ml of a main fermentation medium containing 18% dextrin, 2% glycerin, 3% soybean powder, 2% gluten meal, 0.2% magnesium carbonate and 0.23% sodium hydroxide was prepared and sterilized at 120° C. for 20 minutes; 2 ml of the above-described seed culture solution was transplanted, and incubation was initiated at 30° C. with a rotary shaker at 240 rpm. Separately, a 500 ml Sakaguchi flask containing 100 ml of GPY medium (1% glucose, 0.25% peptone and 0.25% yeast extract) was sterilized and prepared. Thereafter, esterase-producing yeast Torulopsis sp. YE-0807L (FERM BP-1158) was inoculated, followed by seed culturing at 30° C. for 2 days. On the first day of the main fermentation of the Y-G19Z strain, 1 ml each of the seed culture solution of the esterase-producing yeast was added and the incubation was continued for 7 days. Subsequent to the second day of the fermentation, 3 flasks were provided for analysis of the concentration of oganomycin E, etc. daily. The concentration of the product was determined by HPLC (column: LS224 (made by Toyo Soda Co., Ltd., 4 mm×500 mm), eluant: 0.02M citric acid (pH 3.2), detection: UV detector 254 nm).

A linear increase of the concentration of oganomycin E was observed as shown by a mean value of the 3 flasks in Table 1 below. Further the concentration reached 60 mM or more on the 7th day.

TABLE 1

| Day of Fermentation | 2 | 3 | 4 | 5 | 6 | 7 |
|---|---|---|---|---|---|---|
| Oganomycin E (mg/ml) | 3 | 7 | 12 | 16 | 20 | 25 |

EXAMPLE (b) (Production of N-phthaloyloganomycin E)

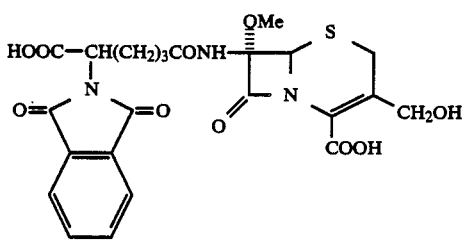

(i) Infrared absorption spectrum $\nu_{max}^{KBr} cm^{-1}$ 2950, 3000-2400 (carboxylic acid), 1770 ($\beta$-lactam), 1710, 1600, 1390.

(ii) Mass spectrum (FAB) for $C_{23}H_{23}N_3O_{10}S$ MW 533 m/Z 556 (M+ +Na).

(iii) Nuclear magnetic resonance spectrum (in DMSO-$d_6$, TMS internal standard);

$\delta$ppm: 1.46 (2H, m), 2.20 (4H, m), 3.34 (3H, s), 4.84 (1H, s), 7.88 (4H, s), 9.00 (1H, s).

EXAMPLE (c)

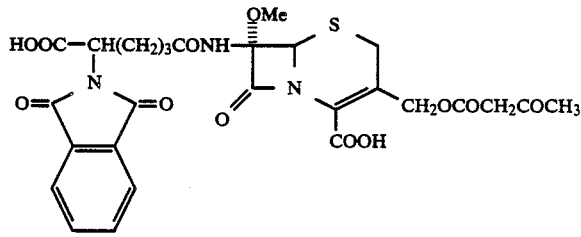

To one liter of the fermentation filtrate containing 4327 a/ml of oganomycin E were gradually added 50 g of N-carboethoxyphthalimide in 300 ml of acetone under stirring at room temperature and while adjusting the pH of the mixture between 9.2 and 9.5 with 40% potassium carbonate, the mixture was allowed to stand for 90 minutes.

After the reaction finished, the mixture was adjusted to pH 4.0 with 4N HCl and passed through 1 l of SP 207 resin (Mitsubishi Chemical Industries Ltd.). After washing with water, the adsorbed N-phthaloyloganomycin E was eluted with approximately 1 l of 50% acetone-water, the eluate adjusted to a pH not less than 4.0. The eluate was concentrated to approximately 300 ml under reduced pressure and extracted twice with 300 ml of methylethylketone at pH 4.5 to remove impurities. Further, the eluate was adjusted to pH 2.5 under ice-water cooling and extracted twice with 300 ml of methylethylketone to extract off almost the desired compound.

The methylethylketone solution containing N-phthaloyloganomycin E was dried over anhydrous sodium sulfate and the solvent distilled off at 30° C. under reduced pressure to give 21 g of dried N-phthaloyloganomycin E having 14% of purity.

One g of the dried N-phthaloyloganomycin E thus obtained was dissolved in 2 ml of 50% acetone-water and spotted on a TLC plate (silica gel 60F254; Merck) and developed with a solvent (ethyl acetate:methanol:water=6:3:1) at 4° C. for 2 hours. After developing, the UV spot portion including N-phthaloyloganomycin E was scratched, and to the resulting silica gel was added 20 ml of distilled water to perform elution for 30 minutes under stirring. The eluate was centrifuged and concentrated at 30° C. under reduced pressure. Approximately 1 ml of the concentrated solution was subjected to a TLC plate once again as above-mentioned and 2-3 ml of the concentrated solution thus obtained put into a sample bottle and lyophilized to give 40 mg of the lyophilized product. The physico-chemical properties of the thus obtained N-phthaloyloganomycin E are shown below:

After 20 g of the dried residue containing N-phthaloyloganomycin E were dissolved in 5 ml of triethylamine and 40 ml of dichloromethane, to the solution were added under stirring 2 ml of diketene and the mixture was allowed to react for an hour at room temperature. After reaction, the reaction mixture was evaporated to dryness under reduced pressure. To the residue were added 50 ml of distilled water and 50 ml of ethyl acetate, the resulting mixture was shaken at pH 5.5 for 3 minutes and the aqueous layer containing N-phthaloyl-3-acetoacetoxymethyloganomycin E separated. To the layer was again added 50 ml of ethyl acetate and the desired product was almost extracted at pH 2.0 adjusted with 4N HCl. The ethyl acetate layer containing the desired product was dried over anhydrous sodium sulfate, and evaporated to dryness at 30° C. under reduced pressure to yield 3.3 g of the dried residue of N-phthaloyl-3-acetoacetoxy-methyloganomycin E having 51% purity.

To the dried N-phthaloyl-3-acetoacetoxymethyloganomycin E was added 1 ml of 50% acetone-water and the mixture spotted on a TLC plate (silica gel 60 F254; Merck) and developed with a solvent (ethyl acetate:methanol:water=6:3:1) at 4° C. for 2 hours. After developing, the UV-spot portion showing the presence of N-phthaloyl-3-acetoacetoxymethyloganomycin E was scratched and to the resulting silica gel was added 20 ml of distilled water to eluate for 30 minutes under stirring. The eluate was centrifuged and concentrated at 30° C. under reduced pressure. The solution concentrated to approximately 1 ml was spotted on a TLC plate and treated again as described above. Two-three ml of the concentrated solution thus obtained was introduced into a sample bottle and lyophilized to give 70 mg of the product.

The physico-chemical properties of the product are shown below:

(i) Infrared absorption spectrum $\nu_{max}^{KBr} cm^{-1}$ 2950, 2900-2700, 1760 ($\beta$-lactam), 1705, 1608, 1390.

(ii) Mass spectrum (FAB) for $C_{27}H_{27}N_3O_{12}S$ MW 617 m/Z 640 (M+ +Na).

(iii) Nuclear magnetic resonance spectrum;

$\delta$ppm: 1.44 (2H, m), 2.18 (3H, s), 2.23 (2H, m), 3.34 (3H, s), 2.95, 3.36 (2H, dd), 3.59 (2H, s), 4.40 (1H, m), 4.79, 4.94 (2H, dd), 4.89 (1H, s), 7.85 (4H, s), 9.01 (1H, s).

REFERENCE EXAMPLE (Production of N-phthaloyloganomycin G)

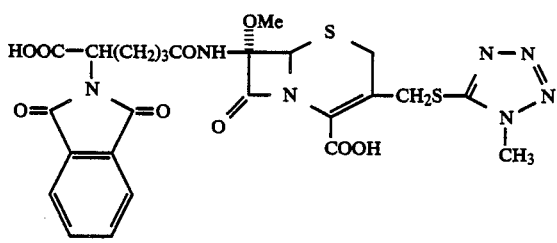

After dissolving 3 g of the dried residue containing N-phthaloyl-3-acetoacetoxymethyloganomycin E prepared in Example (c) in 20 ml of 0.05M phosphate buffer solution of pH 6.0, to the solution were added 0.12 g of sodium salt of 1-methyl-1,2,3,4-tetrazol-5-thiol.dihydrate and 6 ml of acetone and allowed to stand in a water bath at 47° C. By sampling after 5 hours and analyzing quantitatively using, as an authentic standard, N-phthaloyloganomycin G previously identified, production of 1.2 g of N-phthaloyloganomycin G was confirmed.

The solution of 0.5 g of resulting N-phthaloyloganomycin G in 1 ml of 50% acetone-water was spotted on a TLC plate (silica gel 60 F254; Merck) and developed with a solvent (ethyl acetate:methanol:water=6:3:1) at 4° C. for 2 hours. After development, the UV-spot portion showing the presence of N-phthaloyloganomycin G was scratched and the resulting silica gel subjected to elution with 20 ml of distilled water for 30 minutes under stirring. The eluate was centrifuged and concentrated at 30° C. under reduced pressure. The solution concentrated to approximately 2—3 ml was introduced into a sample bottle and lyophilized to yield 220 mg of the lyophilized product. The physicochemical properties of this product are shown below:

(i) Infrared absorption spectrum $\nu_{max}^{KBr} cm^{-1}$ 2950, 3000-2500 (carboxylic acid), 1760 ($\beta$-lactam), 1710, 1600, 1390.

(ii) Mass spectrum (FAB) for $C_{23}H_{25}N_7O_9S_2$ MW 631 m/Z 654 ($M^+ + Na$).

(iii) Nuclear magnetic resonance spectrum (DMSO-$d_6$, TMS internal standard);

$\delta$ppm: 1.44 (2H, m), 2.22 (4H, m), 3.36 (3H, s), 3.36 (2H, q), 3.94 (3H, s), 4.0–4.6 (3H, m), 4.88 (1H, s), 7.86 (4H, s), 9.04 (1H, s).

What is claimed is:

1. 7$\beta$-substituted-3-lower alkanoylacetoxymethyl-7$\alpha$-methoxy-3-cephem-4-carboxylic acid represented by formula (I):

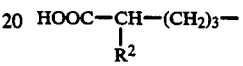

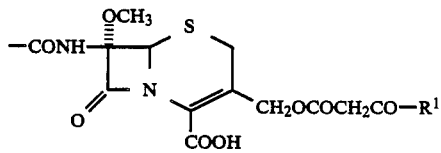

wherein $R^1$ represents a lower alkyl group and $R^2$ represents an amino group which may be protected by an aromatic acyl group or an arylcarbamoyl group or a salt thereof selected from the group consisting of alkali metal salts, alkaline earth metal salts and organic amine salts.

* * * * *